US010131932B2

(12) United States Patent
Qiao et al.

(10) Patent No.: US 10,131,932 B2
(45) Date of Patent: Nov. 20, 2018

(54) METHOD FOR ASSAYING A PROTEASE

(71) Applicants: Shengjun Qiao, Hamilton (CA); Peter Gross, Ancaster (CA)

(72) Inventors: Shengjun Qiao, Hamilton (CA); Peter Gross, Ancaster (CA)

(73) Assignee: McMaster University, Hamilton, Ontario ( * ) Notice: Subject to any disclaimer, the term of this patent is extended or adjusted under 35 U.S.C. 154(b) by 96 days.

(21) Appl. No.: 15/066,509

(22) Filed: Mar. 10, 2016

(65) Prior Publication Data
US 2016/0326569 A1 Nov. 10, 2016

Related U.S. Application Data

(63) Continuation-in-part of application No. PCT/CA2014/000483, filed on Jun. 3, 2014.

(60) Provisional application No. 61/878,826, filed on Sep. 17, 2013.

(51) Int. Cl.
| | |
|---|---|
| *C12N 9/00* | (2006.01) |
| *C12Q 1/56* | (2006.01) |
| *C12Q 1/37* | (2006.01) |
| *G01N 33/542* | (2006.01) |
| *C12N 9/12* | (2006.01) |
| *C12N 9/64* | (2006.01) |
| *C12N 9/74* | (2006.01) |
| *G01N 21/64* | (2006.01) |
| *G01N 33/58* | (2006.01) |

(52) U.S. Cl.
CPC ............ *C12Q 1/56* (2013.01); *C12N 9/12* (2013.01); *C12N 9/6421* (2013.01); *C12N 9/6424* (2013.01); *C12N 9/6429* (2013.01); *C12Q 1/37* (2013.01); *C12Y 207/11001* (2013.01); *C12Y 304/21005* (2013.01); *G01N 21/6428* (2013.01); *G01N 33/542* (2013.01); *G01N 33/581* (2013.01); *C07K 2319/50* (2013.01); *G01N 2021/6432* (2013.01); *G01N 2021/6439* (2013.01); *G01N 2333/974* (2013.01); *G01N 2800/224* (2013.01)

(58) Field of Classification Search
None
See application file for complete search history.

(56) References Cited

FOREIGN PATENT DOCUMENTS

| | | |
|---|---|---|
| WO | 2007/073597 | 7/2007 |
| WO | 2009/035476 | 3/2009 |
| WO | 2010/006605 | 1/2010 |
| WO | 2012/096566 | 7/2012 |

OTHER PUBLICATIONS

Keller and Schilling, Biochimie 92 (2010) 1705-1714.*
International Search Report for PCT/CA2014/000483 dated Mar. 26, 2015, 6 pages.
Zhang, B., "Design of FRET-based GFP probes for detection of protease inhibitors", Biochemical and Biophysical Research Communications. 2004, vol. 323, pp. 674-678.
Kimura, R.H. et al., "Development of a cell-based fluorescence resonance energy transfer reporter for Bacillus anthracis lethal factor protease", Analytical Biochemistry, 2007, vol. 369, pp. 60-70.
Polyak, S.W. et al., "Introduction of spacer peptides N-terminal to a cleavage recognition motif in recombinant fusion proteins can improve site specific cleavage", Protein Engineering, 1997, vol. 10, No. 6, pp. 615-619.
Ai, H-W. et al., "Fluorescent protein FRET pairs for ratiometric imaging of dual biosensors", Nature Methods, May 2008, vol. 5, No. 5, pp. 401-403.
Drake, C.R. et al., "Activatable optical probes for the detection of enzymes", Curr. Org. Synth. Aug. 2011, vol. 8, No. 4, pp. 498-520.
Jones, Matthew A. et al., "Phototropin receptor kinase activation by blue light", Plant Signaling & Behaviour, Jan. 1, 2008, pp. 44-46.
Gellman, Samuel H., "Minimal model systems for [beta]-sheet secondary structure in proteins", Current Opinion in Chemical Biology, vol. 2, No. 6, Jan. 1, 1998, pp. 717-725.

* cited by examiner

*Primary Examiner* — Jeanette M Lieb
(74) *Attorney, Agent, or Firm* — Gowling WLG (Canada) LLP

(57) ABSTRACT

A method of determining generation of an activated protease in a biological sample is provided. The method comprises the steps of exposing a biological sample to a substrate for the activated protease, wherein the substrate comprises a detectable label linked to a cleavage sequence for the activated protease by C-terminal and N-terminal spacers that form a beta-sheet, and wherein the detectable label emits a first signal associated with the substrate and second signal associated with a cleaved product; and determining the generation of the activated protease by measuring the change in the first or second signal over time.

20 Claims, 17 Drawing Sheets

Specification includes a Sequence Listing.

a: buffer
b: rivaroxaban 5 μg/L
c: rivaroxaban 25 μg/L
d: rivaroxaban 50 μg/L a: buffer
b: apixaban 25 μg/L
c: apixaban 100 μg/L
d: apixaban 400 μg/L
e: apixaban 1000 μg/L a: buffer
b: dabigatran 25 µg/L
c: dabigatran 100 µg/L
d: dabigatran 400 µg/L a: thrombin
b: thrombin + α2 macroglobulin
c: thrombin + PPAck
d: thrombin + α2 macroglobulin + PPAck a: human alpha-thrombin
b: human RA thrombin
c: human gamma-thrombin

Figure 13

```
atggtgagcaagggcgaggagctgttcaccggggtggtgcccatcctggtcgagctggacggcgacgtaaacggccacaagttcagc
gtgcgcggcgagggcgagggcgatgccaccaacggcaagctgaccctgaagttcatctgcaccctccggcaagctgcccgtgccctgg
cccaccctcgtgaccaccctgtcttacggcgtgcagtgcttcgcccgctaccccgaccacatgaagcagcacgacttcttcaagtccgcc
atgcccgaaggctacgtccaggagcgcaccatctccttcaaggacgacggcagctacaggacccgcgccgaggtgaagttcgagggc
gacaccctggtgaaccgcatcgagctgaagggcatcgacttcaaggaggacggcaacatcctggggcacaagctggagtacaacatg
aacgtgtgggacgcgtatatcacggccgacaagcagaagaacggcatcaaagcgaacttcaagatcgagcacaacgtcgaggacggc
ggcgtgcagctcgccgacgcgtaccagcagaacacccccatcggcgacggctccgtgctgctgcctgacaaccactacctgagcttcc
agagcaagctgttcaaagaccccaacgagcagcgcgatcacatggtcctgctggagttcgttaccgccgccgggatcactaccgtcact
cctatcaagctggtgccaaggggtgtcaacctgacgatcaagttcatcatcaaagagttcatgcgcttcaaggtgcgcatggagggctcca
tgaacggccacgagttcgagatcgagggcgagggcgagggccgcccctacgagggcacccagaccgccaagctgaaggtgaccaa
gggcggcccctgcccttcgcctgggacatcctgtcccccagttcatgtacggctccaaggcgtacgtgaagcaccccgccgacatcc
ccgattacaagaagctgtccttccccgagggcttcaagtgggagcgcgtgatgaacttcgaggacggcggtctggtgaccgtgacccag
gactcctccctgcaggacggcacgctgatctacaaggtgaagatgcgcggcaccaacttcccccccgacggccccgtaatgcagaaga
agaccatgggctgggaggcctccaccgagcgcctgtaccccgcgacggcgtgctgaagggcgagatccaccaggccctgaagctg
aaggacggcggccactacctggtggagttcaagaccatctacatggccaagaagcccgtgcaactgcccggctactactacgtggaca
ccaagctggacatcacctcccacaacgaggactacaccatcgtggaacagtacgagcgctccgagggccgccaccacctgttcctggg
gcatggcaccggcagcaccggcagcggcagctccggcaccgcctcctccgaggacaacaacatggccgtcatcaaagagttcatgcg
cttcaaggtgcgcatggagggctccatgaacggccacgagttcgagatcgagggcgagggcgagggccgcccctacgagggcaccc
agaccgccaagctgaaggtgaccaagggcggccccctgcccttcgcctgggacatcctgtcccccagttcatgtacggctccaaggc
gtacgtgaagcaccccgccgacatccccgattacaagaagctgtccttccccgagggcttcaagtgggagcgcgtgatgaacttcgagg
acggcggtctggtgaccgtgacccaggactcctccctgcaggacggcacgctgatctacaaggtgaagatgcgcggcaccaacttccc
ccccgacggccccgtaatgcagaagaagaccatgggctgggaggcctccaccgagcgcctgtaccccgcgacggcgtgctgaagg
gcgagatccaccaggccctgaagctgaaggacggcggccactacctggtggagttcaagaccatctacatggccaagaagcccgtgc
aactgcccggctactactacgtggacaccaagctggacatcacctcccacaacgaggactacaccatcgtggaacagtacgagcgctcc
gagggccgccaccacctgttcctgtacggcatggacgagctgtacaag
``` a: storage at ambient temperature for 22 days
b: storage at 4C for 22 days
c: storage at -20C for 22 days

D)

| Parameter | Interclass Correlation (ICC) (Donner and Wells) | Confidence interval of ICC |
| --- | --- | --- |
| Time to peak | 0.89 | 0.60-0.98 |
| Peak height | 0.67 | 0.16-0.95 |
| Area-under-the-curve | 0.83 | 0.08-0.94 |

Solid line: usual condition
Short dashed line: with hTF antibody (25 μg/mL)
Long dashed line: with corn trypsin inhibitor (200 μg/mL)

Figure 17

| Enzyme | Substrate | Km (µM) | kcat (fl/min·nM)* | Kcat/Km (fl/nM²·min) |
|---|---|---|---|---|
| mouse IIa (3µM) | No beta-sheet spacers | 1.84 | 0.000017 | 0.0092 |
| mouse IIa (10nM) | T13 | 2.6 | 1.89 | 726.9 |
| human IIa (10nM) | T13 | 5.5 | 1.50 | 272.7 |
| human IIa (10nM) | T13 L-I | 10.5 | 3.78 | 360.0 |
| human aPC (100nM) | T13 | 0.16 | 0.0000053 | 0.033 |
| human Xa (2nM) | IEGR with no beta-sheet spacers | 1.84 | 0.022 | 11.9 |
| human Xa (2nM) | (X2) IEGR with beta-sheet spacers | 14.2 | 1.79 | 126.1 |

*fl is the change in the fluorescence ratio used to calculate initial reaction rates; its concentration varies directly with the product.

METHOD FOR ASSAYING A PROTEASE

FIELD OF INVENTION

The present invention relates to methods of assaying a protease in a blood sample, and in particular, to methods of determining active protease in a biological sample, such as blood, using a novel substrate.

BACKGROUND OF THE INVENTION

The coagulation of blood occurs through a complex series of reactions that function as a biological amplifier and culminate in the conversion of soluble circulating fibrinogen into a fibrin meshwork at the site of a vascular injury, providing stability to a hemostatic plug of platelets. In this system, relatively few initiating substances sequentially and proteolytically activate a cascade of circulating precursor proteins, zymogen clotting or coagulation factors. Among the reactions is the conversion of the zymogen, prothrombin, to the activated enzyme thrombin, which is the pivotal enzyme of the coagulation system. Thrombin is a serine protease that rapidly activates platelets, activates other clotting factors, and converts fibrinogen to insoluble fibrin. Thrombin also converts the zymogen FXIII to FXIIIa, which chemically cross-links the fibrin clot.

Abnormalities in the coagulation cascade can have potentially fatal effects, leading to extremes of bleeding disorders and excessive clotting, e.g. thrombosis. In addition, anticoagulant medications cause abnormalities in the coagulation cascade.

The coagulation system may be assessed by activating the cascade and measuring the time it takes for a blood or plasma sample to clot. Clotting times provide clinically useful information, however, they only represent the initial (<5%) thrombin generation. The majority of thrombin is formed after this initial period.

Attempts have been made to quantify the dynamics of thrombin formation. In one such method, a thrombin activator is added to a plasma sample together with a fluorogenic thrombin substrate. Thrombin formed during the clotting reaction consumes the substrate, producing a conversion product that is detected fluorometrically in real time. From these data can be calculated the endogenous thrombin potential (ETP, also referred to as the area-under-the-curve), which indicates how much thrombin has been active and for how long. The data can also be used to calculate lag time (the time to formation of thrombin), the maximal thrombin concentration reached, and the time to the peak thrombin formation. However, this method is unable to measure thrombin generation in whole blood, primarily due to fluorescence signal quenching by components in whole blood including red blood cells. A method to detect thrombin generation in whole blood was subsequently developed which included sequestering the fluorogenic product in a layer (filter paper) such that its fluorescence would not be quenched by red blood cells.

Francis et al., (WO2011094185) describe a method for measuring generation of thrombin in a sample of whole blood as a function of time. The method comprises adding to a sample of whole blood a small peptide fluorogenic substrate and a thrombin activator to form an activated sample. A conversion product is permitted to form in the activated sample. Fluorescence is measured as a function of time from a fluorescent group that is released during the formation of the conversion product with the use of a fluorescence detector. The fluorescence detector operates in an extended range mode and has increased sensitivity. Thrombin generation as a function of time can then be calculated from the measured fluorescence.

These methods of measuring thrombin generation are limited in that they detect free thrombin as well as thrombin that is bound to alpha-2-macroglobulin. In order to obtain an accurate measure of physiologically active thrombin in a blood sample, assays to measure thrombin generation must correct for thrombin bound to alpha-2-macroglobulin. While an assay method has been developed which does not measure thrombin bound to alpha-2-macroglobulin, for example as described U.S. Pat. No. 8,138,308 in which a polymer is attached to a fluorogenic thrombin substrate such that thrombin bound to alpha-2-macroglobulin cannot cleave the substrate, it would be desirable to develop an assay that measures activity or generation of an activated protease in the blood.

SUMMARY OF THE INVENTION

A method of determining the presence and/or generation of a protease in a biological sample has now been developed which utilizes a novel substrate for the protease.

Thus, in one aspect, a method of determining the activity of a protease in a biological sample is provided comprising the steps of: exposing a biological sample to a substrate for the protease, wherein the substrate comprises a detectable label linked to a cleavage sequence for the protease by C-terminal and N-terminal spacers that form a beta sheet, and wherein the detectable label emits a first signal associated with the substrate and second signal associated with a cleaved product; and determining the activity of the protease by measuring the change in the first or second signal over time.

In another aspect, a novel substrate for a protease is provided comprising a detectable label linked to a cleavage sequence for the protease by C-terminal and N-terminal spacers that form a beta-sheet, wherein the detectable label emits a first signal associated with the substrate and second signal associated with a cleaved product.

In a further aspect, a method of monitoring coagulation in a biological sample is provided. The method comprises exposing the biological sample to a substrate for an activated coagulation factor, wherein the substrate comprises a detectable label linked to a cleavage sequence for the activated coagulation factor by C-terminal and N-terminal spacers that form a beta-sheet, and wherein the detectable label emits a first signal associated with the uncleaved substrate and second signal associated with a cleaved substrate product; and monitoring coagulation in the biological sample by measuring the change in the first or second signal over time, wherein a decrease in the first signal or an increase in the second signal is indicative of coagulation and little or no change in the signals, or a decreased rate of change, as compared to a control, is indicative of inhibition of coagulation.

These and other aspects of the invention are described by reference to the following figures.

BRIEF DESCRIPTION OF THE FIGURES

FIG. 13 shows the nucleotide sequence of a substrate in accordance with an embodiment of the invention;

FIG. 17 shows a summary of enzyme kinetic parameters presented for different enzymes and different substrates, according to embodiments of the invention.

DETAILED DESCRIPTION

Figure 1:
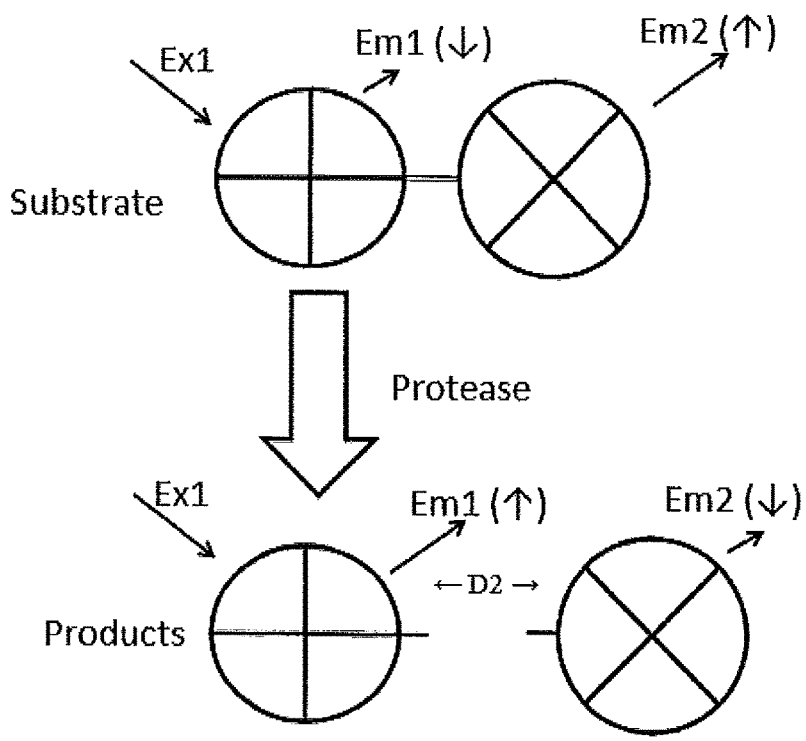
FIG. 1 illustrates a conceptual model of cleavage of a fluorescence resonance energy transfer (FRET)-protein substrate and shows that the fluorescent properties of the products are altered compared to the substrate.

A method of determining the activity or generation of an activated protease in a biological sample as a function of time is provided. The method comprises exposing a biological sample to a substrate for the protease, wherein the substrate comprises a detectable label linked to a cleavage sequence for the protease by C-terminal and N-terminal spacers that form a beta sheet, and wherein the detectable label emits a first signal associated with the substrate and second signal associated with a cleaved substrate product; and determining the activity or generation of activated protease by measuring the change in the first or second signal over time.

The method is useful to determine the presence or generation of an activated protease in a biological sample. As used herein, the term "activated" with respect to a protease refers to the active or functioning form of the protease as opposed to the inactive protease precursor. The biological sample may be any protease-containing biological sample, for example, blood, serum, urine, cerebrospinal fluid, amniotic fluid and other biological samples from a mammal (human or non-human). The present method is particularly advantageous for use with biological samples such as whole blood, plasma, platelet-rich samples or dilutions of any of these. The biological sample may be collected and, if necessary, processed or prepared, using techniques well-established in the art.

The biological sample is exposed to a substrate designed for the target activated protease, for example, an activated serine protease. In one embodiment, the activated protease is an activated blood serine protease, such as an activated coagulation factor. The present method is useful, thus, to measure the generation of an activated coagulation factor such as thrombin, Factor Xa, Factor IXa, Factor VIIa, Factor, XIa, Factor XIIa activated protein C, plasmin, tissue plasminogen activator, urokinase, ADAMTS proteins (a disintegrin and metalloproteinase with a thrombospondin type 1 motif) such as ADAMTS13, or other blood proteases such as matrix metalloproteinases (MMPs) such as MMP1, MMP2, MMP4, MMP9 and MMP12, matriptase, elastase, collagenase, subtilisin, papain and cathepsin B.

Thus, the substrate comprises a cleavage sequence recognized by the target activated protease. In one embodiment, the target protease is an activated coagulation factor such as thrombin. In the determination of activated thrombin generation in accordance with the present method, a thrombin-reactive substrate is utilized incorporating a cleavage sequence recognized by thrombin such as a sequence comprising valine-proline-arginine, e.g. LVPRGVNL (SEQ ID NO: 1) or IVPRGVNL (SEQ ID NO: 2), or sites comprising: phenylalanine-alanine-arginine, phenylalanine-proline-arginine, phenylalanine-homoproline-arginine (S2238), phenylalanine-pipecolic acid-arginine, cyclohexylalanine-alanine-arginine, cyclohexylalanine-proline-arginine, cyclohexylalanine-homoproline-arginine, alanine-alanine-arginine, alanine-proline-arginine, alanine-homoproline-arginine, pyroglutamate-alanine-arginine, pyroglutamate-proline-arginine, pyroglutamate-homoproline-arginine, isoleucine-alanine-arginine, isoleucine-proline-arginine or isoleucine-homoproline-arginine. As one of skill in the art will appreciate, other thrombin cleavage sites may be used, such as those described in Gallwitz et al. (2012). PLoS ONE 7(2): e31756, the contents of which are incorporated herein. Examples include VDPRLIDG (SEQ ID NO: 3), IKPRIVGG (SEQ ID NO: 4), LSPRGVHI (SEQ ID NO: 5), VVPRGVNP (SEQ ID NO: 6), MVPRAVYL (SEQ ID NO: 7), PAPRGYPG (SEQ ID NO: 8), FNPRTFGS (SEQ ID NO: 9), LSPRTFHP (SEQ ID NO: 10), QSPRSFQK (SEQ ID NO: 11), IEPRSFSQ (SEQ ID NO: 12), LDPRSFLL (SEQ ID NO: 13), MTPRSEGS (SEQ ID NO: 14), ARTRARRP (SEQ ID NO: 15), FSARGHRP (SEQ ID NO: 16), GGVRGPRV (SEQ ID NO: 17), GDIRGPRI (SEQ ID NO: 18), LGIRSFRN (SEQ ID NO: 19), LPIKTFRG (SEQ ID NO: 20), WYLRSNNG (SEQ ID NO: 21), LTPRGVRL (SEQ ID NO:22), LWPRGVRL (SEQ ID NO: 23), LTPRGVRD (SEQ ID NO: 24), LTPRGWRL (SEQ ID NO: 25), FNPRT-FGS (SEQ ID NO: 26) and LTPKGVRL (SEQ ID NO: 27).

In another embodiment, the present method may be used to determine the generation of the activated coagulation factor, Factor Xa. In this case, a Factor Xa-reactive substrate is utilized incorporating a cleavage sequence recognized by Factor Xa such as a sequence comprising isoleucine-glutamic acid-glycine-arginine (SEQ ID NO: 28), isoleucine-aspartic acid-glycine-arginine (SEQ ID NO: 29), proline-glutamic acid-glycine-arginine (SEQ ID NO: 30), isoleucine-glutamic acid-glycine-arginine (SEQ ID NO: 31), glutamic acid-glutamic acid-glycine-arginine (SEQ ID NO: 32), glutamic acid-lysine-glycine-arginine (SEQ ID NO: 33) and tyrosine-arginine-glutamic acid-arginine (SEQ ID NO: 34), As one of skill in the art will appreciate, other cleavage sites may be used, such as those described in Hsu et al. (2008). JBC 283(18), the contents of which are incorporated herein, e.g. two arginine residues separated by glycine, alanine, serine, leucine, tyrosine, phenylalanine or tryptophan, WRGTA (SEQ ID NO: 35), LDGRHP (SEQ ID NO: 36), QLGRTT (SEQ ID NO: 37), PRGRVF (SEQ ID NO: 38), SRGRAW (SEQ ID NO: 39) and QMGRSW (SEQ ID NO: 40).

In other embodiments, the method may be used to determine generation of activated urokinase and tissue plasminogen activator (TPA), the substrate for each of which include a cleavage sequence recognized by the activated protease. For example, for urokinase, the cleavage sequence may comprise SGRSA (SEQ ID NO: 41) or SRARKA (SEQ ID NO: 42), for example, while for TPA, the cleavage sequence may comprise FRGRK (SEQ ID NO: 43) or YGRK (SEQ ID NO: 44).

To achieve greater efficiency and specificity for a target protease, such as an activated coagulation factor, a cleavage sequence is selected which is unique for the target protease. For example, with respect to thrombin, while a 3 amino acid cleavage sequence such as valine-proline-arginine is recognized and cleaved by thrombin, to achieve greater sensitivity for thrombin over other proteases, a longer, more complex substrate, e.g. LVPRGVNL or IVPRGVNL, may be utilized. As one of skill in the art will appreciate, the cleavage site may be modified at one or more of its amino acid residues, for example, to include a derivatized R-group which does not adversely effect its use as a substrate, but which may enhance the utility of the cleavage site, e.g. improve specificity.

The cleavage sequence is not particularly limited with respect to length except that the cleavage sequence is a length that permits detection of substrate and cleaved substrate product to occur and a size that permits interaction between the beta sheet spacer sequences to permit beta sheet formation. Thus, the cleavage sequence, in one embodiment may comprise from about 3 to about 20 amino acids, for example, from about 3 to 15 amino acids such as from 3 to 10 amino acids.

The cleavage sequence is linked to a detectable label having a first detectable signal when linked to the substrate and a second detectable signal following cleavage of the substrate. In one embodiment, the detectable label is based on fluorescence resonance energy transfer (FRET). The label, thus, comprises a donor fluorophore that has a first emission spectrum, and an acceptor fluorophore that exhibits a second emission spectrum on cleavage of the substrate which is different from the emission spectrum of the donor fluorophore. Examples of suitable donor/acceptor fluorophore pairs for use in the present method include, but are not limited to, mAmetrine and tdTomato, mTFP1 and mCitrine, TagBFP and TagGFP2, TagGFP2 and TagRFP, CFP and DsRed, GFP and DsRed, CFP and YFP, eCFP and mCitrine, Clover and mRuby2 and eGFP and superREACh.

The detectable label may also be a small molecule FRET pair including, for example, Fluorescein and Tetramethylrhodamine, IAEDANS and Fluorescein, EDANS and Dabcyl, Fluorescein and Fluorescein, BODIPY FL and BODIPY FL, Fluorescein and (QSY 7 or QSY 9), Alexa Fluor 350 and QSY 35, (Alexa Fluor 488 or Alexa Flour 546) and (QSY 35 or QSY 7 or QSY 9), Alexa Fluor 555 and (QSY 7 or QSY 9), Alexa Fluor 568 and (QSY 7 or QSY 9 or QSY 21) and (Alexa Fluor 594 or Alexa Fluor 647) and QSY 21.

The utility of a detectable FRET label is illustrated in FIG. 1. Generally, the fluorescence of the cleavage reaction changes over time as the FRET-protein substrate is cleaved by the target activated protease. Cleavage of the cleavage sequence (which links the two fluorescent proteins, "+" and "x" of the FRET label) increases the distance between the two fluorescent proteins. Excitation at wavelength Ex1 excites the donor fluorescent protein ("+"), which emits light at wavelength Em1. When an acceptor fluorescent protein ("x") is in close proximity (D1), the acceptor protein accepts the energy and emits light at wavelength Em2 and very little light is emitted at wavelength Em1. However, following cleavage of the substrate by the protease and formation of cleaved fluorescent products, the distance between the fluorescent proteins increases (D2) and the fluorescence characteristics of the proteins change. As shown, following cleavage, wavelength Ex1 excites the cleaved donor protein ("+") and, given the cleavage of the donor protein from the acceptor protein and the increased distance between the donor and acceptor, Em1 light emitted by the donor increases (compared to that in the uncleaved substrate) while the acceptor protein is distanced from excitation and Em2 emission decreases. Thus, in the substrate, Em2 emission is greater, while in the cleaved product, Em1 emission is greater.

To permit protease access to the cleavage sequence within the substrate, the cleavage sequence is linked at one end to the donor fluorophore, and at the other end, to the acceptor fluorophore, via N- and C-terminal spacers that interact to form a beta-sheet structure, including parallel and anti-parallel sheets. The spacers may incorporate beta-sheet forming sequences from, for example, a LOV domain (LOV stands for light, oxygen and voltage) of a LOV-containing protein. Examples of proteins having a LOV domain include phototropin-1, phototropin-2, and the following proteins identified by deposit accession no. 4VY11, BMEII0679, B8GYF7, Q7USG5, Q881J7, Q34627, O34627, A3PI49, A6W4X7, Q8XT61, AOL2H7, Q31NI4, Q2NB98, O48963, Q9C9W9 and Q01371.

Sequences from beta-sheet structures which are suitable for use as N- and C-terminal spacers are those sequences which are sufficient to form a beta sheet that permits distinguishable detection of the uncleaved substrate and/or the cleaved product, e.g. beta-sheet sequences which permit the emission of a first signal associated with the uncleaved substrate, e.g. provides a distance between the donor and acceptor fluorophores to enable emission of a first signal which is different from a second signal associated with a cleaved substrate product.

In one embodiment, the beta-sheet spacer sequences are derived from the beta-sheet of phototropin-1 or phototropin-2, e.g. H-beta and I-beta sequence. The spacer sequences are selected such that the N- and C-terminal spacers interact to form a beta-sheet. In addition, the spacers are of a length to permit sufficient detection of the substrate, e.g. by FRET, to yield a first signal, e.g. emission spectrum, and/or the second signal of the cleaved substrate product which is distinct from the first signal. Non-limiting examples of N-terminal spacers for use in the substrate include 5-6 amino acids of the H-beta sequence of phototropin-2 (PFWNLLTVTPIK) (SEQ ID NO: 45), such as TVTPIK (SEQ ID NO: 46) or VTPIK (SEQ ID NO: 47). An example of a C-terminal spacer is the I-beta sequence (TIKFI) (SEQ ID NO: 48). As one of skill in the art will appreciate, the N- and C-terminal spacers are interchangeable, thus, the I-beta sequence may be used as the N-terminal spacer and H-beta sequence may be used as the C-terminal spacer. In addition to the beta-sheet sequence, the spacers may include modified R groups, or inserted sequence, that may facilitate formation of a beta-sheet structure, or otherwise enhance the utility of the substrate, while not interfering with beta-sheet formation and detection of uncleaved and cleaved substrate product such that the signal of each is distinguishable.

The present substrate may be prepared using recombinant technology. For example, as is well-established in the art, a nucleic acid construct encoding the cleavage sequence and linking beta-sheet spacer sequences, with sequence encoding the detectable label, if appropriate, may be prepared and inserted into an expression vector for expression by a host organism, e.g. bacterial or mammalian cells.

Alternatively, cleavage sequence can readily be prepared using standard, solid-phase peptide synthesis methods (SPPS), either manually or using peptide synthesis instruments, as one of skill in the art will appreciate. The linking beta-sheet spacer sequence may be synthesized together with the cleavage sequence, or synthesized separately and subsequently linked thereto using known techniques. Modifications such as those described above, may also be readily accomplished using well-established chemistry. Once a selected cleavage sequence is prepared, it may be purified using standard purification techniques to the required degree to meet standards for use. The detectable label may be synthesized together with the cleavage and spacer sequences, if appropriate to do so, or may be synthesized separately and then linked to the cleavage sequence via the beta-sheet linker sequences using known techniques.

Thus, the present method involves exposing a biological sample, e.g. whole blood, to an activated protease substrate, such as an activated coagulation factor substrate in accordance with the present invention, e.g. a resonance energy transfer (FRET) protease substrate. The activated protease generated within the sample, e.g. thrombin, cleaves the FRET protein substrate, at the cleavage sequence, into two separate proteins. As described, the first signal associated with the uncleaved substrate and the second signal associated with the cleaved product are different and thereby permit detection of the generation of activated protease. In other words, as the cleavage reaction occurs within the sample, the emission of the first signal decreases and the emission of the second signal increases.

The present method may be used to determine generation of an activated protease in an extracted sample, and may also be used for in vivo determinations. The latter may be conducted using imaging techniques known in the art for use in vivo, e.g. that permit FRET-based imaging in vivo, whereby the substrate is administered to the bloodstream of a mammal, e.g. human or non-human mammal, and cleaved and/or uncleaved substrate circulating in the body are detectable using such imaging.

The present method is useful to detect a deficiency or inhibition of a selected protease, such as an activated coagulation factor, in a sample or directly in a patient. If the first emission signal associated with the uncleaved substrate remains constant over time, and/or there is little or no increase in the emission of the second signal associated with the cleaved substrate product, or a slower rate of emission of the second signal, as compared with the normal or control rate over time, then this is indicative of a deficiency of the protease or inhibition of the protease. As one of skill in the art will appreciate, "normal" or "control" refers to the result that would be obtained in a sample from a healthy individual that does not include any substance that would interfere with the result. Such deficiency or inhibition may, for example, be indicative of disease or other undesirable condition. Where the protease is an activated coagulation factor, such as thrombin, and there is lack of emission of a signal associated with the cleaved substrate product, this may be indicative of a condition such as a hemophilia, other acquired congenital clotting factor deficiencies, overactive natural anticoagulants (such as antithrombin Pittsburgh), diffuse intravascular coagulation (DIC) and consumption or dilutional coagulapathy. Alternatively, it may be due to the presence of anticoagulant within the sample such as, for example, apixaban, rivaroxaban, dabigatran and heparin. In this regard, the present method may be used to monitor the levels of an anticoagulant in a patient over time.

The present method may be used to detect the tendency of a blood sample to clot by monitoring generation of activated coagulation factor. If the first emission signal associated with the coagulation factor substrate remains constant over time, and there is an increase in the emission of the second signal associated with the cleaved substrate product, or an increase in the rate of emission of the second signal compared to the normal or control rate, then this is indicative of an increased tendency of the blood to clot. This may be indicative of disease or other undesirable condition such as stroke, acute coronary syndromes, rheumatoid arthritis, states of high estrogen (e.g. estrogen supplementation, in vitro fertilization, oral contraceptive medications), chronic obstructive lung disease and other conditions such as those described in Brummel-Zeidins, JTH (2013).

The present method may also be used to screen potential therapeutic compounds for their ability to alter the generation of an activated protease, for example, in whole blood, which are useful to treat conditions such as those above-described, in which there is a deficiency or over-expression of an activated protease. In the case of activated coagulation factors, such therapeutic compounds may be anticoagulant compounds or coagulant-inducing compounds.

The present method advantageously permits the determination of activated protease generation, e.g. thrombin generation, in a biological sample such as blood with no required sample preparation, e.g. sample dilution or any other alteration of the sample. In addition, the determination can be conducted with standard range detection devices, such as standard range fluorescent devices.

The present method is also beneficial in that it may be used to detect activated clotting factor, such as thrombin, but does not detect clotting factor that is inhibited or bound by an inhibitor such as alpha 2-macroglobulin.

Embodiments of the invention are described in the following examples which are not to be construed as limiting.

EXAMPLE 1

Preparation of a Beta-sheet Thrombin Substrate

A FRET-protein substrate for thrombin was prepared as described in Ai et al. 2008. Nat. Methods, v. 5, no. 5, 401-403 expressed from a plasmid. The construct was designed for expression in mammalian cells to measure thrombin activity in the cell, and encoded a linker sequence specific for cleavage by thrombin (LVPRGVNL). The protein coding sequence thus consisted of a FRET donor (mAmetrine), the thrombin cleavage site (LVPRGVNL) and a FRET acceptor (tdTomato as a dimer). The protein coding sequence was then cloned into a modified vector for expression in *E. coli* BL21 (DE3). Modifications to the vector included mutating an inherent thrombin cleavage site that was in the vector. The expression level of the resulting FRET-protein substrate was low. Mouse thrombin cleaved this FRET-protein substrate but very slowly, too slowly be useful. The Km was 1.8 µM and the efficiency (kcat/Km) was 0.0092 fl/nM$^2$·min.

Figure 2:
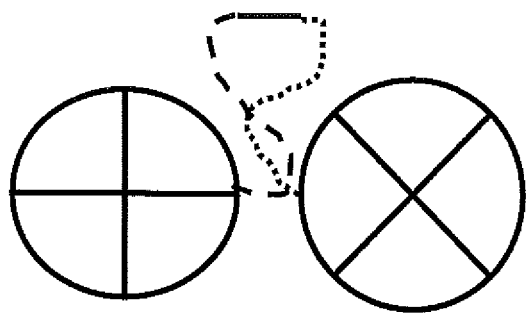
FIG. 2 illustrates a FRET-protein substrate comprising beta-sheet sequence on either side of the cleavage sequence in accordance with an aspect of the invention.

The FRET-protein substrate was then modified by separating the thrombin cleavage sequence from the fluorescent proteins by inserting spacer sequences from the beta-sheet of phototropin-2, e.g. H-beta and I-beta, as illustrated conceptually in FIG. 2. For the N-terminal of the cleavage sequence, insertions of six and twelve amino acids from H-beta were evaluated. For the C-terminal of the cleavage sequence, insertion of I-beta was evaluated. Thrombin cleaved the protein when the N-terminal spacer was TVT-PIK of H-beta, and the C-terminal spacer was TIKFI of I-beta. The coding sequence for this substrate is shown in FIG. 13. In addition expression of the FRET-protein substrate by the bacteria was evident with the insertion of these sequences.

Thrombin cleavage sequences, VPRG (SEQ ID NO: 49) and LVPRGVNL were evaluated. The cleavage sequence, LVPRGVNL, exhibited stronger expression associated with cleavage by thrombin. The approximate Km of the substrate including this cleavage sequence (the "T13" substrate) was determined to be 5.5 µM for human thrombin, and 2.6 µM for mouse thrombin. The efficiency (kcat/Km) of T13 for mouse thrombin was 726.9 fl/nM$^2$·min, which is an increase of more than 79,000-fold in efficiency over the substrate without the beta-sheets. Modifying the first leucine, L, in the thrombin cleavage site, LVPRGVNL, to isoleucine, I (e.g. IVPRGVNL) resulted in an increased the Km for human thrombin of 10.5 µM, but also an increased Vmax, to result in an overall increase in efficiency of about 1.3 fold over the T13 substrate.

EXAMPLE 2

Monitoring Thrombin in a Purified System

Figure 3:
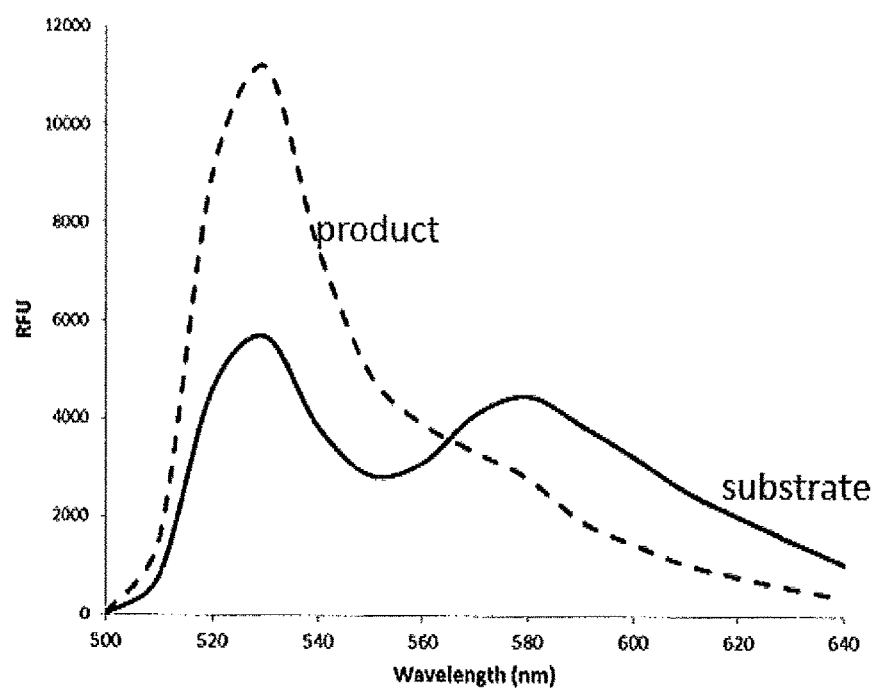
FIG. 3 shows an emission spectra plot of the FRET-protein substrate (solid line), and the FRET-protein substrate after incubation with thrombin for 60 minutes in buffer (the product) after excitation at 406 nm.

The emission spectra of the FRET-protein substrate for thrombin (T13) was obtained on a fluorescence spectrophotometer, Spectramax M5e as shown in FIG. 3. Emission spectrum for the substrate (0.62 µM) was obtained before incubation with thrombin (shown in FIG. 3 as a solid line). Emission spectrum for the cleaved product following incubation with thrombin (45 nM) for 60 minutes in buffer (PIPES) is shown by the dashed line in FIG. 3. Additional testing by SDS-PAGE and Western blotting revealed that no substrate remained in the product.

Figure 4:
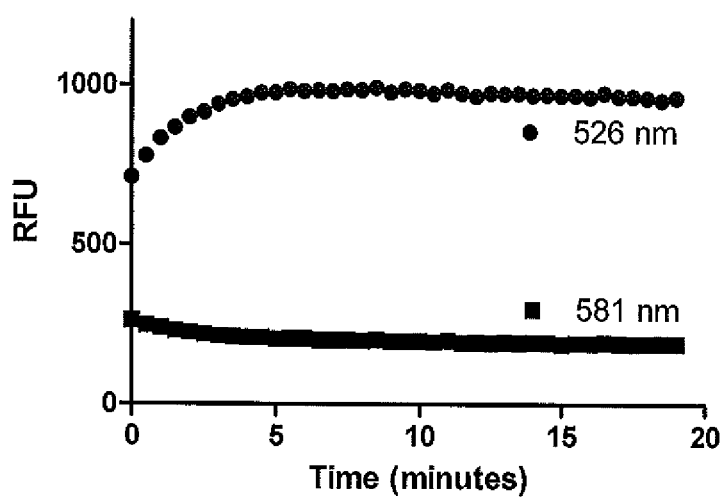
FIG. 4 illustrates emission spectra that show following excitation at 406 nm, the emission at 526 nm increases and the emission at 581 nm decreases over time when thrombin is combined with a FRET-protein substrate.
Figure 5:
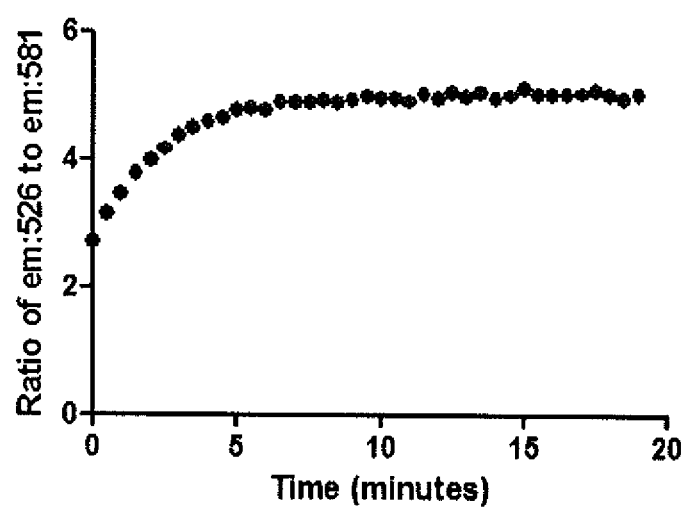
FIG. 5 illustrates the increasing ratio of the emission at 526 nm to that at 581 nm of the mixture of FIG. 4 indicating the conversion of substrate to product.

Emission spectra overtime were determined as shown in FIG. 4. Human thrombin (45 nM) was added to the T13 FRET-protein substrate (0.62 µM) in buffer (PIPES buffer 200 µL, final volume), and after excitation at 406 nm, the emission at 526 nm goes up and the emission at 581 nm goes down indicating conversion of substrate to product. FIG. 5 illustrates the ratio of the emission at 526 nm to that at 581 nm, showing that, over time, this ratio increases indicating the conversion of substrate to product.

EXAMPLE 3

Monitoring Thrombin Generation in a Blood Sample

Figure 6:
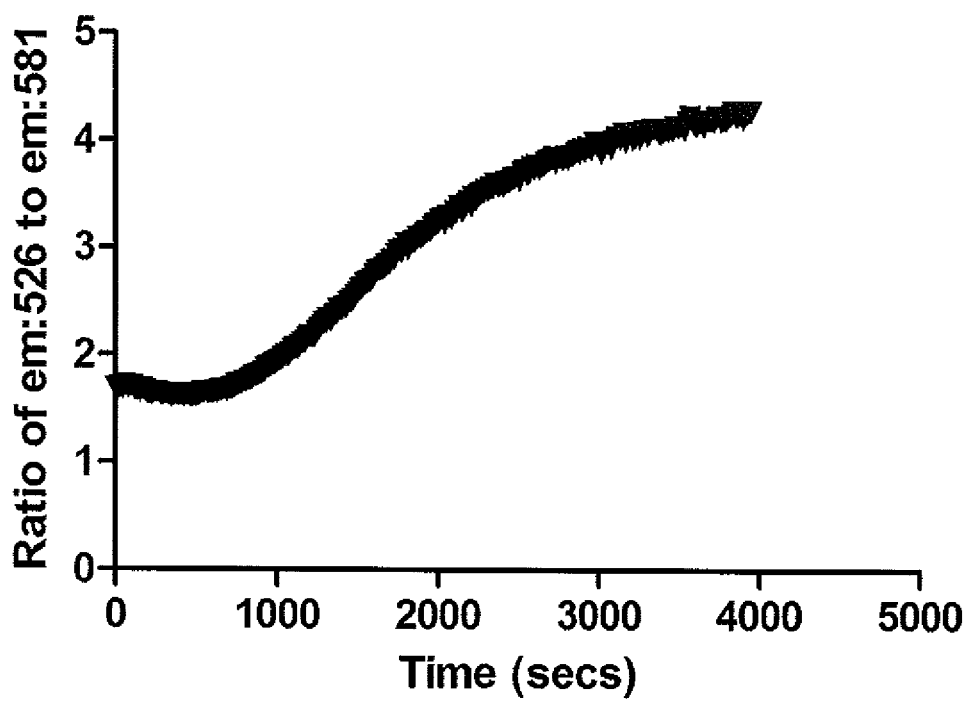
FIG. 6 illustrates ratio of the emission at 526 nm to that at 581 nm of a FRET-protein substrate (8 μL in Piper buffer, 4.6 μM final concentration) added to 12 μL of unanticoagulated human blood.

In this experiment, 12 µL of unanticoagulated human blood, obtained from a finger prick of a healthy human donor, was added to a plastic vessel (NUNC, Polystyrene, 384 well plate) containing the T13 FRET-protein substrate (8 µL in PIPES buffer, 4.6 µM final concentration) within 30 seconds of lancing the finger. Results were obtained on a fluorescence spectrophotometer, as above, temperature controlled to 37° C. Initially, as the mixture warms, the ratio of emission at 526 nm:581 nm decreases slightly, but then increases, initially sharply to a plateau as shown in FIG. 6. Additional testing revealed by SDS-PAGE and Western blotting, that no intact substrate remained in the product at the end of the 12000 seconds.

Figure 7:
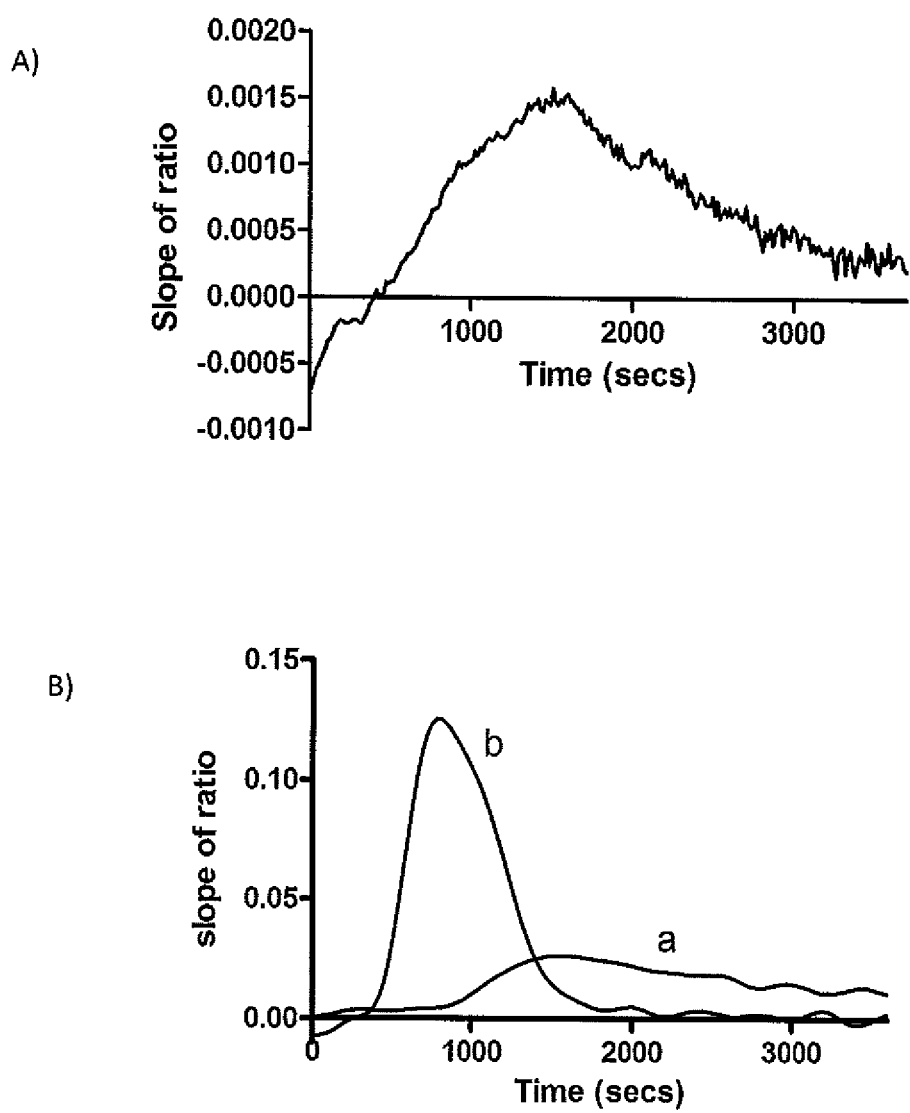
FIG. 7 graphically illustrates A) the slope (smoothed) of the ratio of FIG. 6, and B) compares the graph of A) to that obtained using less dilute substrate in unanticoagulated human blood.

The slope (first derivative) of the ratio was then determined using a mathematical program such as Excel or GraphPad Prism as shown in FIG. 7A. The curve of the slope of the ratio is smoothed using 20 neighbours using a mathematical program (Excel or GraphPad Prism). This is the typical appearance of a thrombin generation curve in plasma. Parameters that could be used to describe this curve include, but are not limited to, peak height, time to peak, lag time, maximal upslope, and area-under-the curve to a certain time point. FIG. 7B compares a) 12 µL blood combined with FRET-protein substrate (final conc. 4.6 µM) to final volume of 20 µL to b) 20 µL blood combined with FRET-protein substrate (final conc. 5.1 µM) to a final volume of 22.5 µL. The time-to-peak and lag-time are shortened and the peak height, maximal upslope and area-under-the-curve are increased in the latter where the blood is less dilute.

EXAMPLE 4

Monitoring Thrombin Generation in the Presence of Anticoagulant

Figure 8:
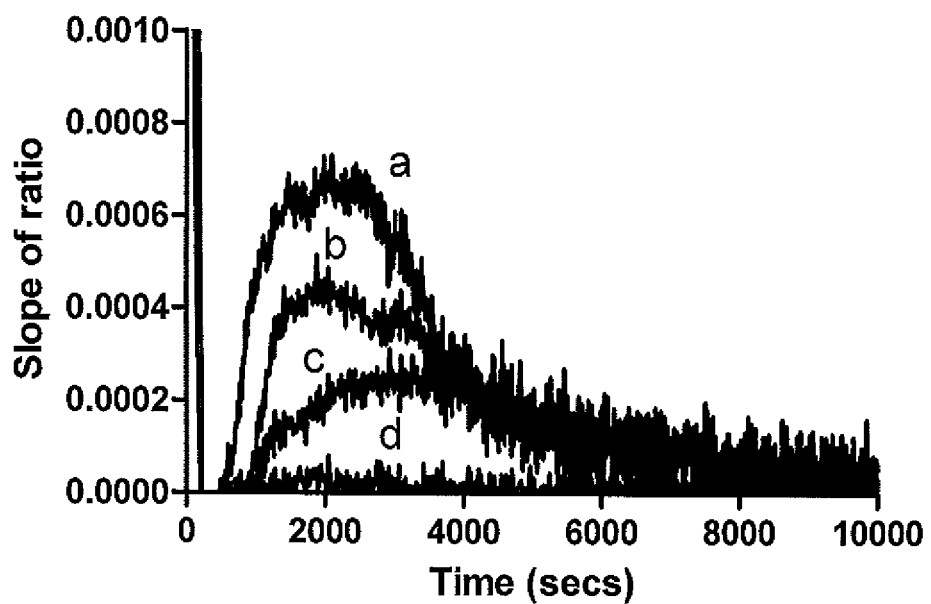
FIG. 8 shows the effect of buffer (a) and various concentrations of rivaroxaban (b)-(d) on thrombin generation in whole blood.

The effect of rivaroxaban on thrombin generation in the blood was determined. Unanticoagulated blood was taken from a finger prick of a healthy volunteer. The blood was added to a plastic vessel containing the FRET-protein substrate (0.62 µM) and rivaroxaban at various concentrations (to a final concentration of 5 µg/L, 25 µg/L and 50 µg/L). As shown in FIG. 8, rivaroxaban alters the shape of the "slope of the ratio curve". Specifically, increasing amounts of rivaroxaban decrease thrombin generation as shown by decreased peak height, maximal upslope and area-under-the-curve.

Figure 9:
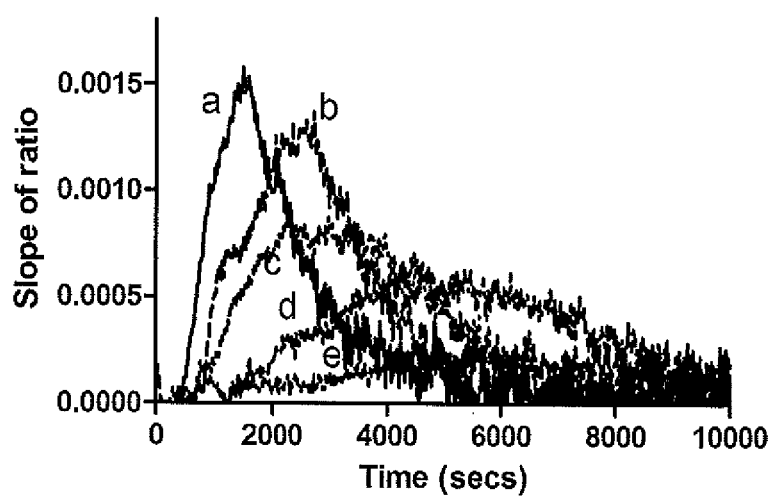
FIG. 9 shows the effect of buffer (a) and various concentrations of apixaban (b)-(e) on thrombin generation in whole blood.

The effect of apixaban on thrombin generation in the blood was also determined. Blood was added to FRET-protein substrate and various concentrations of apixaban was (to a final concentration of 25 µg/L, 100 µg/L, 400 µg/L and 1000 µg/L). Apixaban also alters the shape of the "slope of the ratio curve". Specifically, increasing amounts of apixaban decreases thrombin generation as shown in FIG. 9 by decreased peak height, maximal upslope and the area-under-the-curve. Apixaban is also shown to increase the time to peak.

Figure 10:
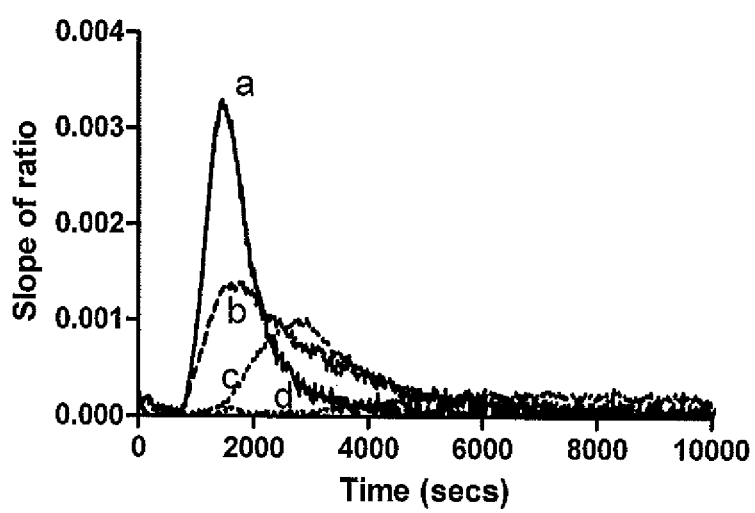
FIG. 10 shows the effect of buffer (a) and various concentrations of dabigatran (b)-(d) on thrombin generation in whole blood.

The effect of dabigatran on thrombin generation in the blood was also determined. Blood was added to FRET-protein substrate and various concentrations of apixaban was (to a final concentration of 25 µg/L, 100 µg/L and 400 µg/L). Dabigatran also alters the shape of the "slope of the ratio curve". Specifically, increasing amounts of dabigatran decreases thrombin generation as shown in FIG. 10 by decreased peak height, maximal upslope and the area-under-the-curve. Dabigatran is also shown to increase the time to peak at higher concentrations.

EXAMPLE 5

Effect on Thrombin Activity of Alpha-2-macroglobulin and Substrates

Figure 11:
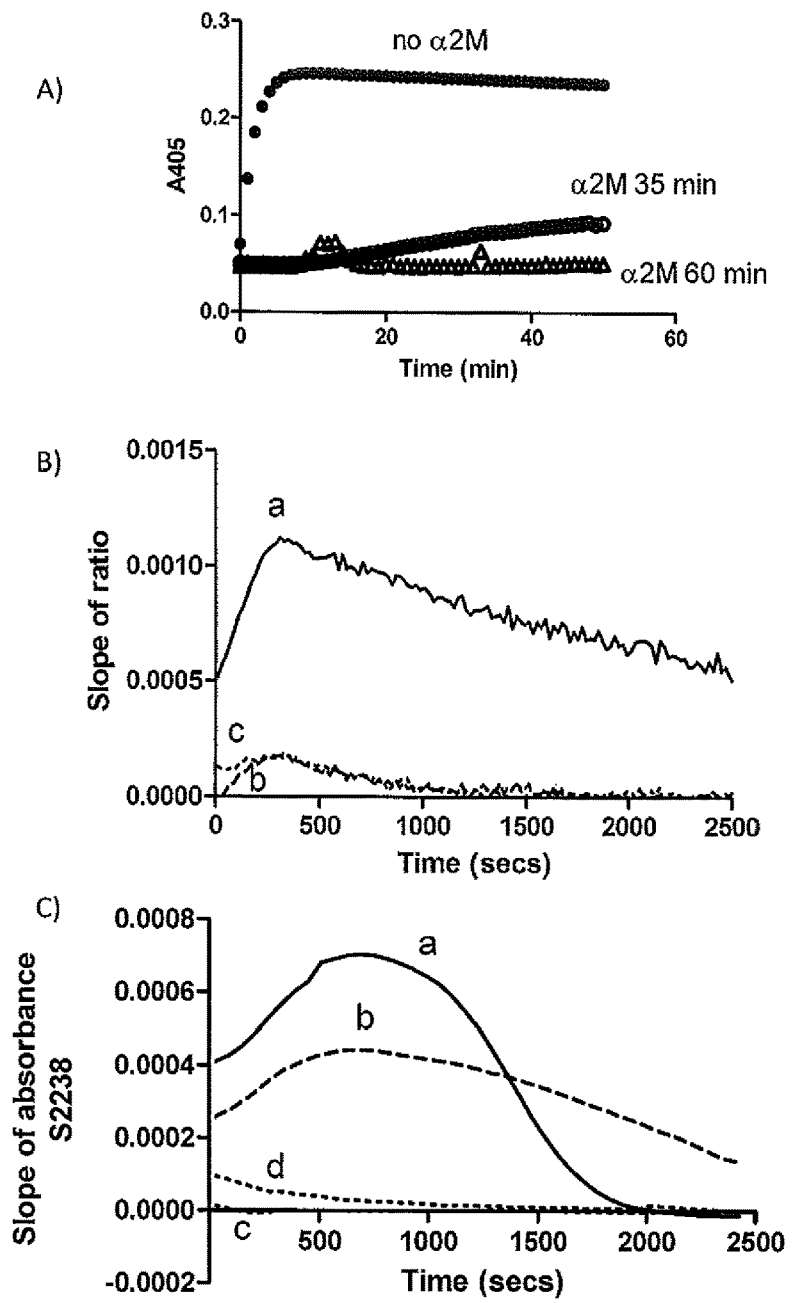
FIG. 11 shows the effect of alpha-2-macroglobulin on thrombin activity (A), compares thrombin activity (B) in the absence (a) and presence of alpha-2-macroglobulin (b) and a thrombin inhibitor (PPACk)(c), both in the presence of fibrinogen, and compares thrombin activity (C) in the absence (a) and presence of alpha-2-macroglobulin (b), PPAck (c) and a both alpha-2-macroglobulin and PPAck (d) in the presence of the thrombin substrate, S2238.
Figure 12:
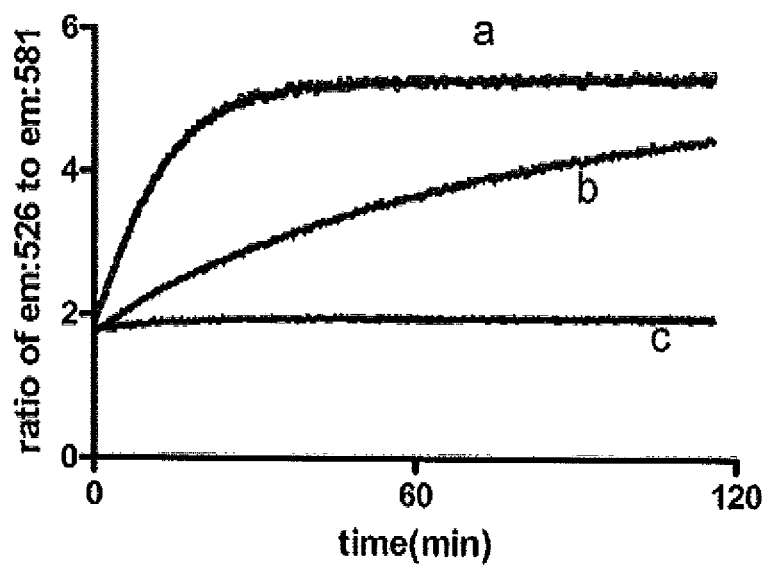
FIG. 12 graphically compares the activity of different forms of thrombin (a)-(c) on thrombin generation measured using a FRET-protein substrate.

The effect of alpha-2-macroglobulin on thrombin activity was determined. Thrombin (2 nM) and calcium (5 mM) were combined in PIPES buffer. Clotting was initiated by the addition of fibrinogen (3 µM). Clotting was measured by monitoring turbidity 405 nm using a spectrometer. The fibrinogen clotted within 10 minutes and remained clotted. Pre-incubation of the thrombin with alpha-2-macroglobulin (0.2 µM) for 35 minutes reduced clotting and pre-incubation of the thrombin with alpha-2-macroglobulin for 60 minutes inhibited clotting as shown in FIG. 11A.

The effect of the FRET-protein substrate on the thrombin activity in the absence and presence of alph-2-macroglobulin was then determined. Following addition of either thrombin (as above), thrombin incubated with alpha-2-macroglobulin for 60 minutes (as above) or thrombin incubated for 60 minutes with the thrombin inhibitor, PPAck (D-FPR-chloromethyl ketone, 20 µM), thrombin activity was determined. Thrombin was inhibited by either alpha-2-macroglobulin or PPAck, as shown by the reduction in the slope of the ratio for each (FIG. 11B). This confirms that thrombin is inhibited by alpha-2-macroglobulin and does not cleave the T13 substrate.

The effect of thrombin substrate, S2238, on thrombin activity in the presence and absence of alpha-2-macroglobulin was then determined. Following addition of thrombin (as above), thrombin incubated with alpha-2-macroglobulin for 60 minutes (as above), thrombin incubated with PPAck (as above) for 60 minutes, or thrombin incubated with alpha-2-macroglobulin (0.2 µM) and PPAck (20 µM) for 60 minutes, to S2238, thrombin activity was determined. There is little inhibition of thrombin when incubated with alpha-2-macroglobulin, but substantial inhibition when thrombin is inhibited by PPAck or the combination of PPAck and alpha-2-macroglobulin, as indicated by the reduced slope of absorbance shown in FIG. 11C. This indicates, as is known, that S2238 does not distinguish between thrombin and thrombin bound by alpha-2-macroglobulin.

EXAMPLE 6

Activity of Different Forms of Thrombin on FRET-protein Substrate

Various forms of thrombin (each at 5 nM) were added to the T13 FRET-protein substrate, in PIPES buffer (200 µL), as described in FIG. 5. The thrombin forms included normal human thrombin, known as alpha-thrombin; RA thrombin, a variant of thrombin in which three arginine amino acids (93, 97 and 101) in a substrate binding region called exosite II are mutated to alanine; and gamma-thrombin, a variant lacking a substrate binding region called exosite I. The T13 FRET-protein substrate was cleaved by alpha-thrombin, cleaved somewhat by RA thrombin and was not cleaved by gamma-thrombin. This indicates that T13 binds exosite I of thrombin (alpha-thrombin), and that binding to exosite II is not required for cleavage by thrombin (alpha-thrombin).

EXAMPLE 7

Storage of a FRET-protein Substrate

Figure 14:
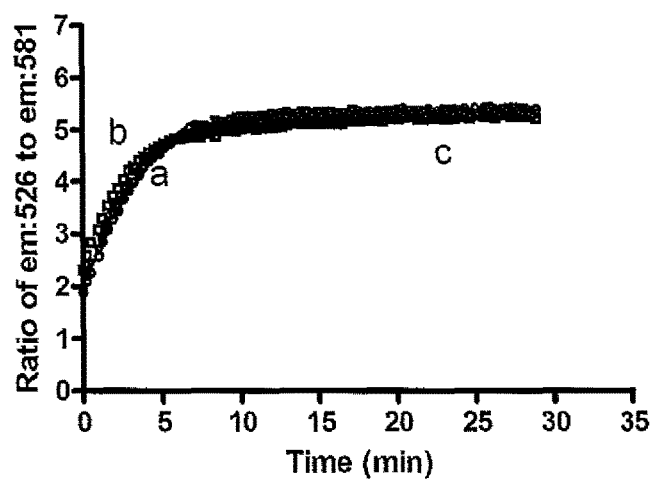
FIG. 14 shows the effect of various storage conditions (a)-(c) on a substrate in accordance with an embodiment of the invention.

The effect of storage conditions on the T13 FRET-protein substrate was determined. The substrate was stored at a concentration of 2 mg/mL in PIPES buffer, at either ambient temperature, 4° C., or −20° C. for 22 days. As shown in FIG. 14, storage of the substrate at various temperatures does affect cleavage by thrombin.

EXAMPLE 8

Figure 15:
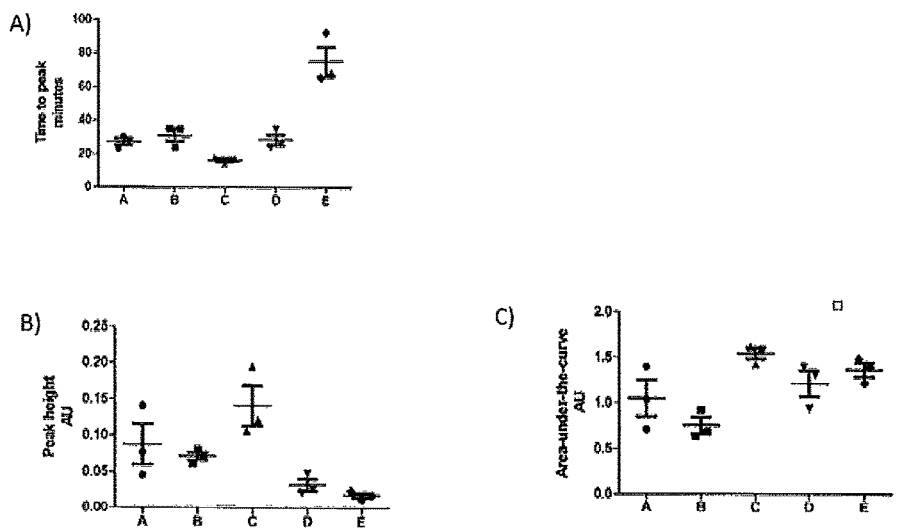
FIG. 15 graphically compares thrombin generation using a FRET-protein substrate in unanticoagulated whole blood from 5 human volunteers by peak height (A), time to peak (B), and area-under-the-curve (C), and by interclass correlation (D)

Variation of Thrombin Generation in Unanticoagulated Whole Blood within and Between Healthy Volunteers Thrombin generation was determined in unanticoagulated whole blood from 5 separate healthy human volunteers (A, B, C, D, E) on three separate occasions. The peak height, time to peak, and area-under-the-curve were analyzed and compared. Variation in thrombin generation between volunteer blood samples was seen as expected, but blood samples from the same volunteer were shown to be quite similar (see FIGS. 15A, B and C). The latter is quantified by the interclass correlation (Donner and Wells, Biometrics, v. 42, no. 2, 401-412) as shown in FIG. 15D. A higher number indicates a better correlation; of the parameters analyzed, the time to peak varies least within the same volunteer.

EXAMPLE 9

Inhibition of Thrombin Generation in Unanticoagulated Whole Blood

Figure 16:
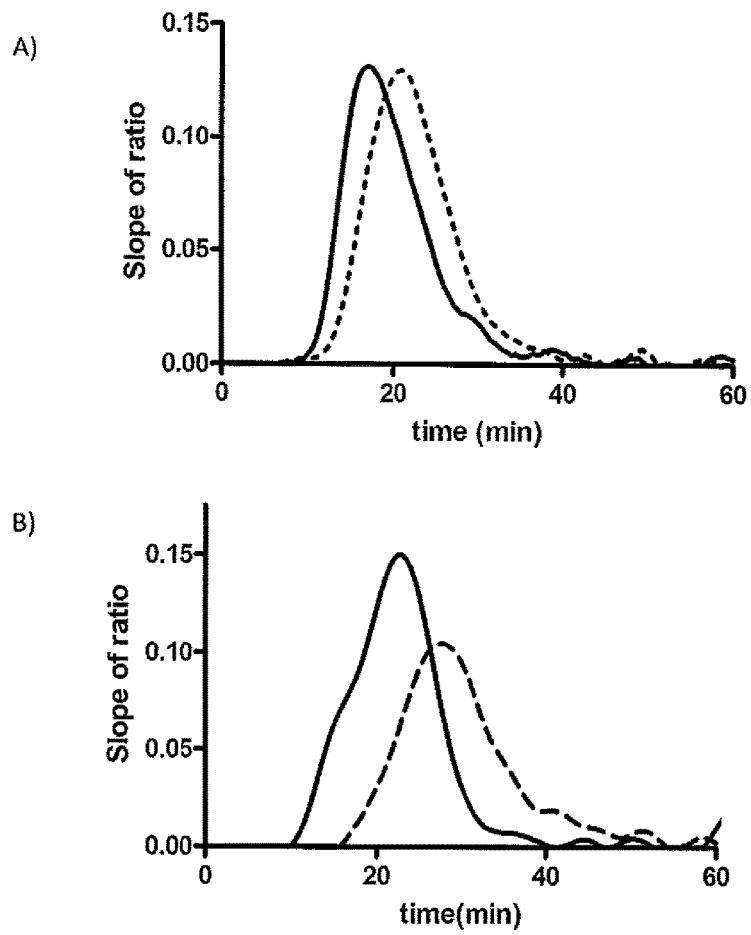
FIG. 16 shows the effect of different thrombin inhibitors on thrombin generation and activity in blood (A/B)

The effect of different inhibitors on thrombin generation and activity, in blood, was determined, using the method described in Example 3. To determine which of the intrinsic or extrinsic pathway of coagulation was initiating the clotting in unanticoagulated whole blood in the vessel, inhibitors of these two pathways were used. The effect of an anti-human tissue factor antibody (hTF, 25 µg/mL final concentration) was shown to have a slight delaying effect on thrombin activity as shown by a plot of slope of ratio (see FIG. 16A), suggesting a small contribution of the extrinsic pathway in initiating coagulation. The effect of corn trypsin inhibitor (a factor XIIa inhibitor, 200 µg/mL final concentration) was shown to both delay and reduce thrombin generation as seen by a lowering and delay of the peak of slope or ratio, suggesting a contribution of the intrinsic pathway in initiating coagulation in this assay.

EXAMPLE 10

Kinetics for Various Enzyme/Substrate Pairs

Enzyme kinetics of different enzymes and substrates were determined as shown in FIG. 17. Varying concentrations of each of the substrates (0.1 to 37 µM) were added to each enzyme in PIPES buffer (200 µL, final volume), and experiments were performed as in Example 2. The initial rate of ratio increase (taken before less than 10% of the total increase had occurred) was plotted against the substrate concentration. Using Michaelis-Menten kinetics (Graphpad PRISM) the Vmax and Km were determined. Vmax was converted to kcat to compare the different substrates. The parameter kcat/Km is a measure of enzyme efficiency. T13 is a much more efficient substrate for mouse thrombin (IIa) than is the substrate lacking beta-sheet spacers. Mouse thrombin is slightly more efficient in cleaving T13 than is human thrombin. The L to I substitution at P4 in T13 (T13 L-I) only slightly increases human thrombin's cleavage efficiency. Human activated protein C (aPC) is less efficient in cleaving T13 than human thrombin.

A substrate to detect factor Xa cleavage, X2, was also developed in accordance with the invention. In this case, the T13 substrate was modified to include a site for Factor Xa cleavage (namely, IEGR) instead of LVPRGVNL. This substrate was referred to as "X2". X2 was cleaved by human Factor Xa with similar efficiency to that of the cleavage of T13 by human thrombin. In contrast, human Factor Xa cleaved a substrate with the IEGR cleavage site but without beta-sheet spacers at one tenth the efficiency.

What is claimed is:

1. An activated protease substrate comprising a detectable label linked to a cleavage sequence for the protease by C-terminal and N-terminal spacers that form a beta-sheet, wherein the detectable label emits a first signal associated with the substrate and second signal associated with a cleaved substrate product.

2. The substrate of claim 1, comprising a cleavage sequence selected from the group consisting of thrombin, Factor Xa, Factor IXa, Factor VIIa, Factor, XIa, Factor XIIa, activated protein C, plasmin, tissue plasminogen activator, urokinase, a disintegrin and metalloproteinase with a thrombospondin type 1 motif (ADAMTS) protein, a matrix metalloproteinase, matriptase, elastase, collagenase, subtilisin, papain and cathepsin B.

3. The substrate of claim 1, comprising a cleavage sequence for an activated coagulation factor.

4. The substrate of claim 1, wherein one of the N- and C-terminal spacers comprises sequence from the I-beta sheet and the other spacer comprises sequence from the H-beta sheet of phototropin 1 or 2.

5. The substrate of claim 4, wherein one of the spacers has the sequence TVTPIK and the other spacer has the sequence TIKFI.

6. The substrate of claim 1, wherein the detectable label is a FRET donor and acceptor pair.

7. The substrate of claim 6, wherein the FRET donor and acceptor pair is selected from the group consisting of mAmetrine and tdTomato, mTFP 1 and mCitrine, TagBFP and TagGFP2, TagGFP2 and TagRFP, CFP and DsRed, GFP and DsRed, CFP and YFP, eCFP and mCitrine, Clover and mRuby2 and eGFP and superREACh.

8. The substrate of claim 1, wherein the first signal is emission at 581 nm, and the second signal is emission at 526 nm.

9. The substrate of claim 1, wherein the detectable label is the FRET donor and acceptor pair, mAmetrine and tdTomato, the cleavage sequence is a thrombin cleavage sequence and one of the beta-sheet spacers has the sequence, TVTPIK and the other has the sequence, TIKFI.

10. A method of determining generation of an activated protease in a biological sample comprising the steps of:
exposing a biological sample to a substrate for the activated protease, wherein the substrate comprises a detectable label linked to a cleavage sequence for the activated protease by C-terminal and N-terminal spacers that form a beta-sheet, and wherein the detectable label emits a first signal associated with the substrate and second signal associated with a cleaved substrate product; and
determining the generation of activated protease factor by measuring the change in the first or second signal over time.

11. The method of claim 10, wherein the biological sample is selected from whole blood, plasma or a platelet-rich sample.

12. The method of claim 11, wherein the substrate comprises a cleavage sequence for an activated serine protease.

13. The method of claim 12, wherein the substrate comprises a cleavage sequence for an activated coagulation factor.

14. The method of claim 10, wherein one of the N- and C-terminal spacers comprises sequence from the I-beta sheet and the other spacer comprises sequence from the H-beta sheet of phototropin 1 or 2.

15. The method of claim 14, wherein one of the beta sheet spacers has the sequence TVTPIK and the other beta sheet spacer has the sequence TIKFI.

16. The method of claim 10, wherein the detectable label is a FRET donor and acceptor pair selected from the group consisting of mAmetrine and tdTomato, mTFP1 and mCitrine, TagBFP and TagGFP2, TagGFP2 and TagRFP, CFP and DsRed, GFP and DsRed, CFP and YFP, eCFP and mCitrine, Clover and mRuby2 and eGFP and superREACh.

17. The method of claim 10, wherein the first signal is emission at 581 nm, and the second signal is emission at 526 nm.

18. A method of monitoring coagulation in a biological sample comprising:
exposing the biological sample to a substrate for an activated coagulation factor, wherein the substrate comprises a detectable label linked to a cleavage sequence for the activated coagulation factor by C-terminal and N-terminal spacers that form a beta-sheet, and wherein the detectable label emits a first signal associated with the uncleaved substrate and second signal associated with a cleaved substrate product; and
monitoring coagulation in the biological sample by measuring the change in the first or second signal over time, wherein a decrease in the first signal or an increase in the second signal is indicative of coagulation and little or no change in the signals, or a decreased rate of change, as compared to a control, is indicative of inhibition of coagulation.

19. The method of claim 18, wherein the method is used to monitor anticoagulation in a blood sample as indicated by little or no change in the first or second signals, or a decreased rate of change of the sigals, as compared to a control.

20. The method of claim 18, wherein the substrate comprises a thrombin cleavage sequence, the detectable label is a FRET donor and acceptor pair and the C- and N-terminal spacers comprise beta-sheet sequence from phototropin 1 or 2.

* * * * *

SEQUENCE LISTING

```
<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: cleavage sequence

<400> SEQUENCE: 1

Leu Val Pro Arg Gly Val Asn Leu
1               5

<210> SEQ ID NO 2
<211> LENGTH: 8
<212> TYPE: PRT
<213> ORGANISM: Artificial Sequence
<220> FEATURE:
<223> OTHER INFORMATION: cleavage sequence

<400> SEQUENCE: 2

Ile Val Pro Arg Gly Val Asn Leu
1               5

<210> SEQ ID NO 3
<211> LENGTH: 8
<212> TYPE: PRT
<213> ORGANISM: Artificial Sequence
<220> FEATURE:
<223> OTHER INFORMATION: cleavage sequence

<400> SEQUENCE: 3

Val Asp Pro Arg Leu Ile Asp Gly
1               5

<210> SEQ ID NO 4
<211> LENGTH: 8
<212> TYPE: PRT
<213> ORGANISM: Artificial Sequence
<220> FEATURE:
<223> OTHER INFORMATION: cleavage sequence

<400> SEQUENCE: 4

Ile Lys Pro Arg Ile Val Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: cleavage sequence

<400> SEQUENCE: 5

Leu Ser Pro Arg Gly Val His Ile
1               5
```

<210> SEQ ID NO 6
<211> LENGTH: 8
<212> TYPE: PRT
<213> ORGANISM: Artificial Sequence
<220> FEATURE:
<223> OTHER INFORMATION: cleavage sequence

<400> SEQUENCE: 6

Val Val Pro Arg Gly Val Asn Pro
1               5

<210> SEQ ID NO 7
<211> LENGTH: 8
<212> TYPE: PRT
<213> ORGANISM: Artificial Sequence
<220> FEATURE:
<223> OTHER INFORMATION: cleavage sequence

<400> SEQUENCE: 7

Met Val Pro Arg Ala Val Tyr Leu
1               5

<210> SEQ ID NO 8
<211> LENGTH: 8
<212> TYPE: PRT
<213> ORGANISM: Artificial Sequence
<220> FEATURE:
<223> OTHER INFORMATION: cleavage sequence

<400> SEQUENCE: 8

Pro Ala Pro Arg Gly Tyr Pro Gly
1               5

<210> SEQ ID NO 9
<211> LENGTH: 8
<212> TYPE: PRT
<213> ORGANISM: Artificial Sequence
<220> FEATURE:
<223> OTHER INFORMATION: cleavage sequence

<400> SEQUENCE: 9

Phe Asn Pro Arg Thr Phe Gly Ser
1               5

<210> SEQ ID NO 10
<211> LENGTH: 8
<212> TYPE: PRT
<213> ORGANISM: Artificial Sequence
<220> FEATURE:
<223> OTHER INFORMATION: cleavage sequence

<400> SEQUENCE: 10

Leu Ser Pro Arg Thr Phe His Pro
1               5

<210> SEQ ID NO 11
<211> LENGTH: 8
<212> TYPE: PRT
<213> ORGANISM: Artificial Sequence
<220> FEATURE:
<223> OTHER INFORMATION: cleavage sequence

<400> SEQUENCE: 11

Gln Ser Pro Arg Ser Phe Gln Lys
1               5

```
<210> SEQ ID NO 12
<211> LENGTH: 8
<212> TYPE: PRT
<213> ORGANISM: Artificial Sequence
<220> FEATURE:
<223> OTHER INFORMATION: cleavage sequence

<400> SEQUENCE: 12

Ile Glu Pro Arg Ser Phe Ser Gln
1               5

<210> SEQ ID NO 13
<211> LENGTH: 8
<212> TYPE: PRT
<213> ORGANISM: Artificial Sequence
<220> FEATURE:
<223> OTHER INFORMATION: cleavage sequence

<400> SEQUENCE: 13

Leu Asp Pro Arg Ser Phe Leu Leu
1               5

<210> SEQ ID NO 14
<211> LENGTH: 8
<212> TYPE: PRT
<213> ORGANISM: Artificial Sequence
<220> FEATURE:
<223> OTHER INFORMATION: cleavage sequence

<400> SEQUENCE: 14

Met Thr Pro Arg Ser Glu Gly Ser
1               5

<210> SEQ ID NO 15
<211> LENGTH: 8
<212> TYPE: PRT
<213> ORGANISM: Artificial Sequence
<220> FEATURE:
<223> OTHER INFORMATION: cleavage sequence

<400> SEQUENCE: 15

Ala Arg Thr Arg Ala Arg Arg Pro
1               5

<210> SEQ ID NO 16
<211> LENGTH: 8
<212> TYPE: PRT
<213> ORGANISM: Artificial Sequence
<220> FEATURE:
<223> OTHER INFORMATION: cleavage sequence

<400> SEQUENCE: 16

Phe Ser Ala Arg Gly His Arg Pro
1               5

<210> SEQ ID NO 17
<211> LENGTH: 8
<212> TYPE: PRT
<213> ORGANISM: Artificial Sequence
<220> FEATURE:
<223> OTHER INFORMATION: cleavage sequence

<400> SEQUENCE: 17

Gly Gly Val Arg Gly Pro Arg Val
1               5
```

```
<210> SEQ ID NO 18
<211> LENGTH: 8
<212> TYPE: PRT
<213> ORGANISM: Artificial Sequence
<220> FEATURE:
<223> OTHER INFORMATION: cleavage sequence

<400> SEQUENCE: 18

Gly Asp Ile Arg Gly Pro Arg Ile
1               5

<210> SEQ ID NO 19
<211> LENGTH: 8
<212> TYPE: PRT
<213> ORGANISM: Artificial Sequence
<220> FEATURE:
<223> OTHER INFORMATION: cleavage sequence

<400> SEQUENCE: 19

Leu Gly Ile Arg Ser Phe Arg Asn
1               5

<210> SEQ ID NO 20
<211> LENGTH: 8
<212> TYPE: PRT
<213> ORGANISM: Artificial Sequence
<220> FEATURE:
<223> OTHER INFORMATION: cleavage sequence

<400> SEQUENCE: 20

Leu Pro Ile Lys Thr Phe Arg Gly
1               5

<210> SEQ ID NO 21
<211> LENGTH: 8
<212> TYPE: PRT
<213> ORGANISM: Artificial Sequence
<220> FEATURE:
<223> OTHER INFORMATION: cleavage sequence

<400> SEQUENCE: 21

Trp Tyr Leu Arg Ser Asn Asn Gly
1               5

<210> SEQ ID NO 22
<211> LENGTH: 8
<212> TYPE: PRT
<213> ORGANISM: Artificial Sequence
<220> FEATURE:
<223> OTHER INFORMATION: cleavage sequence

<400> SEQUENCE: 22

Leu Thr Pro Arg Gly Val Arg Leu
1               5

<210> SEQ ID NO 23
<211> LENGTH: 8
<212> TYPE: PRT
<213> ORGANISM: Artificial Sequence
<220> FEATURE:
<223> OTHER INFORMATION: cleavage sequence

<400> SEQUENCE: 23

Leu Trp Pro Arg Gly Val Arg Leu
1               5

<210> SEQ ID NO 24
```

```
<211> LENGTH: 8
<212> TYPE: PRT
<213> ORGANISM: Artificial Sequence
<220> FEATURE:
<223> OTHER INFORMATION: cleavage sequence

<400> SEQUENCE: 24

Leu Thr Pro Arg Gly Val Arg Asp
1               5

<210> SEQ ID NO 25
<211> LENGTH: 8
<212> TYPE: PRT
<213> ORGANISM: Artificial Sequence
<220> FEATURE:
<223> OTHER INFORMATION: cleavage sequence

<400> SEQUENCE: 25

Leu Thr Pro Arg Gly Trp Arg Leu
1               5

<210> SEQ ID NO 26
<211> LENGTH: 8
<212> TYPE: PRT
<213> ORGANISM: Artificial Sequence
<220> FEATURE:
<223> OTHER INFORMATION: cleavage sequence

<400> SEQUENCE: 26

Phe Asn Pro Arg Thr Phe Gly Ser
1               5

<210> SEQ ID NO 27
<211> LENGTH: 8
<212> TYPE: PRT
<213> ORGANISM: Artificial Sequence
<220> FEATURE:
<223> OTHER INFORMATION: cleavage sequence

<400> SEQUENCE: 27

Leu Thr Pro Lys Gly Val Arg Leu
1               5

<210> SEQ ID NO 28
<211> LENGTH: 4
<212> TYPE: PRT
<213> ORGANISM: Artificial Sequence
<220> FEATURE:
<223> OTHER INFORMATION: cleavage sequence

<400> SEQUENCE: 28

Ile Glu Gly Arg
1

<210> SEQ ID NO 29
<211> LENGTH: 4
<212> TYPE: PRT
<213> ORGANISM: Artificial Sequence
<220> FEATURE:
<223> OTHER INFORMATION: cleavage sequence

<400> SEQUENCE: 29

Ile Asp Gly Arg
1

<210> SEQ ID NO 30
<211> LENGTH: 4
```

```
<212> TYPE: PRT
<213> ORGANISM: Artificial Sequence
<220> FEATURE:
<223> OTHER INFORMATION: cleavage sequence

<400> SEQUENCE: 30

Pro Glu Gly Arg
1

<210> SEQ ID NO 31
<211> LENGTH: 4
<212> TYPE: PRT
<213> ORGANISM: Artificial Sequence
<220> FEATURE:
<223> OTHER INFORMATION: cleavage sequence

<400> SEQUENCE: 31

Ile Glu Gly Arg
1

<210> SEQ ID NO 32
<211> LENGTH: 4
<212> TYPE: PRT
<213> ORGANISM: Artificial Sequence
<220> FEATURE:
<223> OTHER INFORMATION: cleavage sequence

<400> SEQUENCE: 32

Glu Glu Gly Arg
1

<210> SEQ ID NO 33
<211> LENGTH: 4
<212> TYPE: PRT
<213> ORGANISM: Artificial Sequence
<220> FEATURE:
<223> OTHER INFORMATION: cleavage sequence

<400> SEQUENCE: 33

Glu Lys Gly Arg
1

<210> SEQ ID NO 34
<211> LENGTH: 4
<212> TYPE: PRT
<213> ORGANISM: Artificial Sequence
<220> FEATURE:
<223> OTHER INFORMATION: cleavage sequence

<400> SEQUENCE: 34

Tyr Arg Glu Arg
1

<210> SEQ ID NO 35
<211> LENGTH: 5
<212> TYPE: PRT
<213> ORGANISM: Artificial Sequence
<220> FEATURE:
<223> OTHER INFORMATION: cleavage sequence

<400> SEQUENCE: 35

Trp Arg Gly Thr Ala
1               5

<210> SEQ ID NO 36
<211> LENGTH: 6
<212> TYPE: PRT
```

```
<213> ORGANISM: Artificial Sequence
<220> FEATURE:
<223> OTHER INFORMATION: cleavage sequence

<400> SEQUENCE: 36

Leu Asp Gly Arg His Pro
1               5

<210> SEQ ID NO 37
<211> LENGTH: 6
<212> TYPE: PRT
<213> ORGANISM: Artificial Sequence
<220> FEATURE:
<223> OTHER INFORMATION: cleavage sequence

<400> SEQUENCE: 37

Gln Leu Gly Arg Thr Thr
1               5

<210> SEQ ID NO 38
<211> LENGTH: 6
<212> TYPE: PRT
<213> ORGANISM: Artificial Sequence
<220> FEATURE:
<223> OTHER INFORMATION: cleavage sequence

<400> SEQUENCE: 38

Pro Arg Gly Arg Val Phe
1               5

<210> SEQ ID NO 39
<211> LENGTH: 6
<212> TYPE: PRT
<213> ORGANISM: Artificial Sequence
<220> FEATURE:
<223> OTHER INFORMATION: cleavage sequence

<400> SEQUENCE: 39

Ser Arg Gly Arg Ala Trp
1               5

<210> SEQ ID NO 40
<211> LENGTH: 6
<212> TYPE: PRT
<213> ORGANISM: Artificial Sequence
<220> FEATURE:
<223> OTHER INFORMATION: cleavage sequence

<400> SEQUENCE: 40

Gln Met Gly Arg Ser Trp
1               5

<210> SEQ ID NO 41
<211> LENGTH: 5
<212> TYPE: PRT
<213> ORGANISM: Artificial Sequence
<220> FEATURE:
<223> OTHER INFORMATION: cleavage sequence

<400> SEQUENCE: 41

Ser Gly Arg Ser Ala
1               5

<210> SEQ ID NO 42
<211> LENGTH: 6
<212> TYPE: PRT
<213> ORGANISM: Artificial Sequence
```

```
<220> FEATURE:
<223> OTHER INFORMATION: cleavage sequence

<400> SEQUENCE: 42

Ser Arg Ala Arg Lys Ala
1               5

<210> SEQ ID NO 43
<211> LENGTH: 5
<212> TYPE: PRT
<213> ORGANISM: Artificial Sequence
<220> FEATURE:
<223> OTHER INFORMATION: cleavage sequence

<400> SEQUENCE: 43

Phe Arg Gly Arg Lys
1               5

<210> SEQ ID NO 44
<211> LENGTH: 4
<212> TYPE: PRT
<213> ORGANISM: Artificial Sequence
<220> FEATURE:
<223> OTHER INFORMATION: cleavage sequence

<400> SEQUENCE: 44

Tyr Gly Arg Lys
1

<210> SEQ ID NO 45
<211> LENGTH: 12
<212> TYPE: PRT
<213> ORGANISM: Artificial Sequence
<220> FEATURE:
<223> OTHER INFORMATION: beta-sheet sequence

<400> SEQUENCE: 45

Pro Phe Trp Asn Leu Leu Thr Val Thr Pro Ile Lys
1               5                   10

<210> SEQ ID NO 46
<211> LENGTH: 6
<212> TYPE: PRT
<213> ORGANISM: Artificial Sequence
<220> FEATURE:
<223> OTHER INFORMATION: N-terminal spacer

<400> SEQUENCE: 46

Thr Val Thr Pro Ile Lys
1               5

<210> SEQ ID NO 47
<211> LENGTH: 5
<212> TYPE: PRT
<213> ORGANISM: Artificial Sequence
<220> FEATURE:
<223> OTHER INFORMATION: N-terminal spacer

<400> SEQUENCE: 47

Val Thr Pro Ile Lys
1               5

<210> SEQ ID NO 48
<211> LENGTH: 5
<212> TYPE: PRT
<213> ORGANISM: Artificial Sequence
<220> FEATURE:
```

<223> OTHER INFORMATION: C-terminal spacer

<400> SEQUENCE: 48

Thr Ile Lys Phe Ile
1               5

<210> SEQ ID NO 49
<211> LENGTH: 4
<212> TYPE: PRT
<213> ORGANISM: Artificial Sequence
<220> FEATURE:
<223> OTHER INFORMATION: cleavage sequence

<400> SEQUENCE: 49

Val Pro Arg Gly
1

<210> SEQ ID NO 50
<211> LENGTH: 2155
<212> TYPE: DNA
<213> ORGANISM: Artificial Sequence
<220> FEATURE:
<223> OTHER INFORMATION: activated protease substrate

<400> SEQUENCE: 50

```
atggtgagca agggcgagga gctgttcacc ggggtggtgc ccatcctggt cgagctggac      60
ggcgacgtaa acggccacaa gttcagcgtg cgcggcgagg gcgagggcga tgccaccaac     120
ggcaagctga ccctgaagtt catctgcacc tccggcaagc tgcccgtgcc ctggcccacc     180
ctcgtgacca ccctgtctta cggcgtgcag tgcttcgccc gctaccccga ccacatgaag     240
cagcacgact tcttcaagtc cgccatgccc gaaggctacg tccaggagcg caccatctcc     300
ttcaaggacg acggcagcta caggacccgc gccgaggtga agttcgaggg cgacaccctg     360
gtgaaccgca tcgagctgaa gggcatcgac ttcaaggagg acggcaacat cctggggcac     420
aagctggagt acaacatgaa cgtgtgggac gcgtatatca cggccgacaa gcagaagaac     480
ggcatcaaag cgaacttcaa gatcgagcac aacgtcgagg acggcggcgt gcagctcgcc     540
gacgcgtacc agcagaacac ccccatcggc gacggctccg tgctgctgcc tgacaaccac     600
tacctgagct tccagagcaa gctgttcaaa gaccccaacg agcagcgcga tcacatggtc     660
ctgctggagt tcgttaccgc cgccgggatc actaccgtca ctccctatca acctggtgcc     720
aagggggtgtc aacctgacga tcaagttcat catcaaagag ttcatgcgct tcaaggtgcg     780
catggagggc tccatgaacg gccacgagtt cgagatcgag ggcgagggcg agggccgccc     840
ctacgagggc acccagaccg ccaagctgaa ggtgaccaag ggcggccccc tgcccttcgc     900
ctgggacatc ctgtcccccc agttcatgta cggctccaag gcgtacgtga agcacccccgc     960
cgacatcccc gattacaaga agctgtcctt ccccgagggc ttcaagtggg agcgcgtgat    1020
gaacttcgag gacggcggtc tggtgaccgt gacccaggac tcctccctgc aggacggcac    1080
gctgatctac aaggtgaaga tgcgcggcac caacttcccc cccgacggcc ccgtaatgca    1140
gaagaagacc atgggctggg aggcctccac cgagcgcctg taccccgcg acggcgtgct    1200
gaagggcgag atccaccagg ccctgaagct gaaggacggc ggccactacc tggtggagtt    1260
caagaccatc tacatggcca gaagcccgt gcaactgccc ggctactact acgtggacac    1320
caagctggac atcacctccc acaacgagga ctacaccatc gtggaacagt acgagcgctc    1380
cgagggccgc caccacctgt tcctgggcag tggcaccggc agcaccggca gcggcagctc    1440
cggcaccgcc tcctccgagg acaacaacat ggccgtcatc aaagagttca tgcgcttcaa    1500
```

```
ggtgcgcatg gagggctcca tgaacggcca cgagttcgag atcgagggcg agggcgaggg      1560
ccgcccctac gagggcaccc agaccgccaa gctgaaggtg accaagggcg gcccctgcc      1620 cttcgcctgg gacatcctgt cccccagtt catgtacggc tccaaggcgt acgtgaagca      1680
ccccgccgac atcccgatt acaagaagct gtccttcccc gagggcttca gtgggagcg      1740 cgtgatgaac ttcgaggacg gcggtctggt gaccgtgacc caggactcct ccctgcagga      1800
cggcacgctg atctacaagg tgaagatgcg cggcaccaac ttccccccg acggcccgt      1860 aatgcagaag aagaccatgg gctgggaggc ctccaccgag cgcctgtacc cccgcgacgg      1920
cgtgctgaag ggcgagatcc accaggccct gaagctgaag gacggcggcc actacctggt      1980
ggagttcaag accatctaca tggccaagaa gcccgtgcaa ctgcccggct actactacgt      2040
ggacaccaag ctggacatca cctcccacaa cgaggactac accatcgtgg aacagtacga      2100
gcgctccgag ggccgccacc acctgttcct gtacggcatg gacgagctgt acaag          2155
```